United States Patent [19]
Presswood

[11] Patent Number: 5,403,185
[45] Date of Patent: Apr. 4, 1995

[54] DENTAL ARTICULATOR

[76] Inventor: Thomas L. Presswood, 327 Explorer, Austin, Tex. 78734

[21] Appl. No.: 166,607

[22] Filed: Dec. 13, 1993

Related U.S. Application Data

[63] Continuation of Ser. No. 806,490, Dec. 13, 1991, abandoned.

[51] Int. Cl.$^6$ .................. A61C 19/00; A61C 11/00
[52] U.S. Cl. .................................. 433/74; 433/53; 433/57
[58] Field of Search .................. 433/34, 36, 49, 50, 433/53, 54, 57, 60, 74

[56] References Cited

U.S. PATENT DOCUMENTS

| | | | |
|---|---|---|---|
| 2,669,780 | 2/1954 | Mann | 433/53 |
| 2,842,845 | 7/1958 | Carlson | 433/74 |
| 3,436,829 | 4/1969 | Jermyn | 433/74 |
| 3,722,099 | 3/1973 | Jankelson | 433/34 |
| 4,017,972 | 4/1977 | Glenn | 433/74 |
| 4,122,606 | 10/1978 | Roman | 433/74 X |
| 4,200,981 | 5/1980 | Fine | 433/60 |
| 4,245,987 | 1/1981 | Bertoldi | 433/61 |
| 4,265,619 | 5/1991 | Lucki et al. | 433/74 X |
| 4,371,339 | 2/1983 | Zeiser | 433/74 |
| 4,439,151 | 3/1984 | Whelan | 433/74 |
| 4,449,931 | 5/1984 | Saito | 433/34 X |
| 4,708,835 | 11/1987 | Kiefer | 433/74 |
| 4,842,242 | 6/1989 | Huffman | 433/60 |
| 4,865,546 | 9/1989 | Naylor | 433/60 X |
| 4,952,151 | 8/1990 | Metcalfe | 433/74 X |
| 5,026,279 | 6/1991 | Wilkes | 433/74 X |
| 5,098,290 | 3/1992 | Honstein et al. | 433/74 |
| 5,197,874 | 3/1993 | Silva et al. | 433/74 |

FOREIGN PATENT DOCUMENTS 2653743  6/1978  Germany .................. 433/74

Primary Examiner—Nicholas D. Lucchesi
Attorney, Agent, or Firm—Gambrell, Wilson & Hamilton

[57] ABSTRACT

An improved method and apparatus for producing a dental prosthetic with a minimum of time and labor. The preferred embodiment of the invention compresses first and second trays which are hingedly secured to allow articulating movement of the trays with respect to each other. At least one of the trays is provided with a grid having a plurality of holes in a spaced pattern to receive pins for supporting the model. In operation, one of the trays is filled with plaster and the negative impression of the teeth is placed therein. The operator then closes the articulator temporarily to determine the optimum location of the pins with respect to the various teeth marks in the impression. The pins are then inserted into the appropriate holes in the opposing tray, with the pins being parallel to each other. The impression is then filled with plaster and the tray containing the pins is then closed to cause the individual pins to be inserted into the plaster at the predetermined locations. After the plaster is hardened, the upper tray is rotated away from the plaster, with the pins remaining in the aligned position within the impression. The plaster model can then be removed to allow further work to be performed on the teeth of interest.

15 Claims, 6 Drawing Sheets

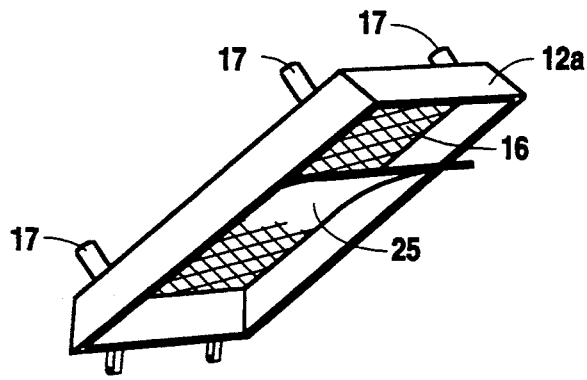
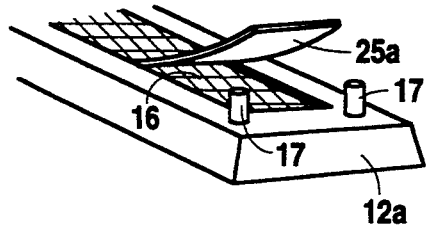
Fig. 3a        Fig. 3b
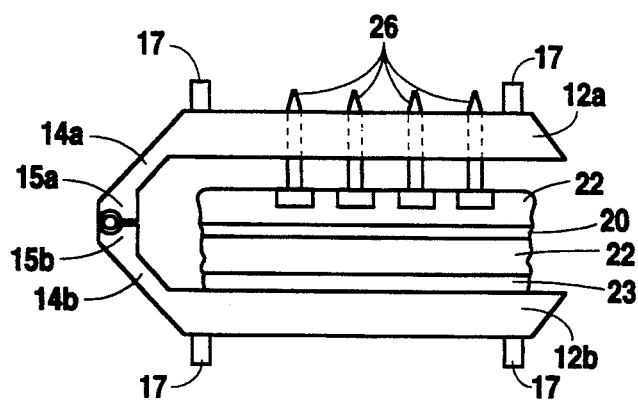
Fig. 4
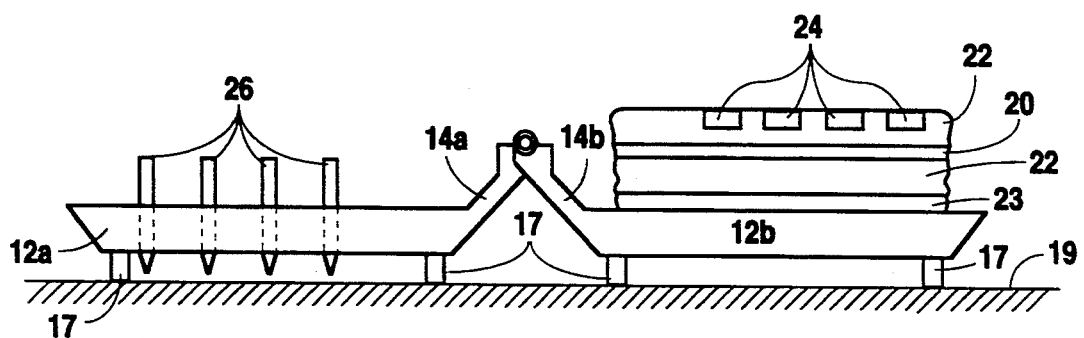
Fig. 5

DENTAL ARTICULATOR

This is a continuation of application Ser. No. 07/806,490, filed on Dec. 13, 1991, both abandoned.

FIELD OF INVENTION

The present invention relates generally to the field of dental prosthetics. More specifically, the present invention provides an improved method and apparatus for positioning pin type supports within a plaster dental model to ensure precise placement of the pins in the areas to be used for producing removable teeth and dies in a working model.

BACKGROUND

In the preparation of false teeth or caps, the dentist will normally prepare a negative impression of the affected tooth or teeth. The negative impression is normally obtained by filling a tray with polymer material and having the patient sink his teeth into the polymer material to create a plurality of depressions or cavities in the polymer material. After the polymer material cures, it is removed from the patient's mouth and hardens to from a semi-permanent impression of the patient's teeth and gum.

The negative impression of the patient's teeth and gums is used as a mold for developing a model of the patient's teeth to facilitate the production of a replacement tooth or other prosthetic. To form a tooth model, the quantity of casting stone, often referred to as die stone, is poured into the negative impression.

In the prior art, the base for the dental mold is made by one of two methods. First, additional hardenable stone, or plaster, is poured within the negative impression to cover the die stone and the retainer with sufficient depth of plaster to form a solid base. After both the die stone and the plaster have hardened, the tray and supported impression material is peeled away to leave a conventional dental model. Alternatively, a patty of yellow stone is formed upon a glass or other smooth surface. The completely cured die stone, with pins in place, is placed thereupon.

In either method, pins are lodged or fixated in the die stone to extend into and slidably engage the plaster. The pins serve the function of maintaining registration of the model tooth with the remaining model when the model tooth is replaced into the model base after a fabrication step.

All of the prior art methods for using dowel pins to produce a working model of the patient's teeth require that the model be removed from the mold at some step of the modeling process. This results in additional technician time and, therefore, adds to the cost of the dental model. In addition, the removal of the model from the mold tends to cause difficulties in obtaining precise alignment of the opposing sides of the model. In view of the foregoing difficulties, there is a need for a dental articulator and mold apparatus which allows a technician to produce a model of a patient's teeth without having to remove the model from the mold. This need is answered by the method and apparatus of the present invention, discussed in greater detail below.

SUMMARY OF INVENTION

The present invention overcomes the difficulties of the prior art by providing an improved method and apparatus for producing a dental prosthetic with a minimum of time and labor. More specifically, the present invention makes it possible to complete a model through articulation without removing the models from the impression. The invention is especially useful for constructing models with "triple tray" type impression trays which take impressions of both sides of a dental bite and also records an accurate bite registration in one step.

The preferred embodiment of the invention comprises first and second trays which are hingedly secured to allow articulating movement of the trays with respect to each other. At least one of the trays is provided with a plurality of apertures in a spaced pattern to receive pins for providing alignment and support of portions of the model during the various processing steps for fabricating an artificial tooth. The pins are releasably secured in the apertures and can easily be removed from the tray by rotating the tray away from the model after the die stone has hardened.

In operation, one of the trays is filled with plaster and the negative impression of the opposing teeth is placed therein. The operator then closes the articulator temporarily to determine the optimum location of the pins with respect to the various teeth marks in the impression. The pins are then inserted into the appropriate apertures in the opposing tray, with the apertures maintaining the pins in an orientation whereby the pins are substantially parallel to each other and substantially perpendicular to the base of the tray. The impression is then filled with die stone and the tray containing the pins is then closed to cause the individual pins to be inserted into the die stone at the predetermined locations. After the die is hardened, the upper tray is rotated away from the plaster, with the pins remaining in the aligned position within the hardened stone. A quantity of plaster is then placed on top of the die stone and in the upper tray. The upper tray is then rotated downwardly to allow the two quantities of plaster to form a base for the working model. When the tray is rotated downwardly the pins are reinserted into the apertures they occupied prior to being secured in the die stone. The impression can then be removed to allow further work to be performed on the working model of the teeth of interest.

BRIEF DESCRIPTION OF THE DRAWINGS

FIG. 3a is a perspective view of one of the trays of the articulator of the present invention illustrating one embodiment of a tray liner to prevent leakage of plaster from the articulator.

FIG. 3b is a perspective view of one of the trays of the articulator of the present invention illustrating an alternate embodiment of a tray liner to prevent leakage of plaster from the articulator.

FIG. 4 is a side view of the dental articulator with the pins positioned in the upper tray at locations corresponding to the teeth of interest.

FIG. 5 is perspective view of the tray assembly with the upper tray rotated away from the lower tray to move the pins away from the tooth impressions to allow the negative impressions to be filled with die stone.

DETAILED DESCRIPTION OF THE PREFERRED EMBODIMENT

Figure 1:
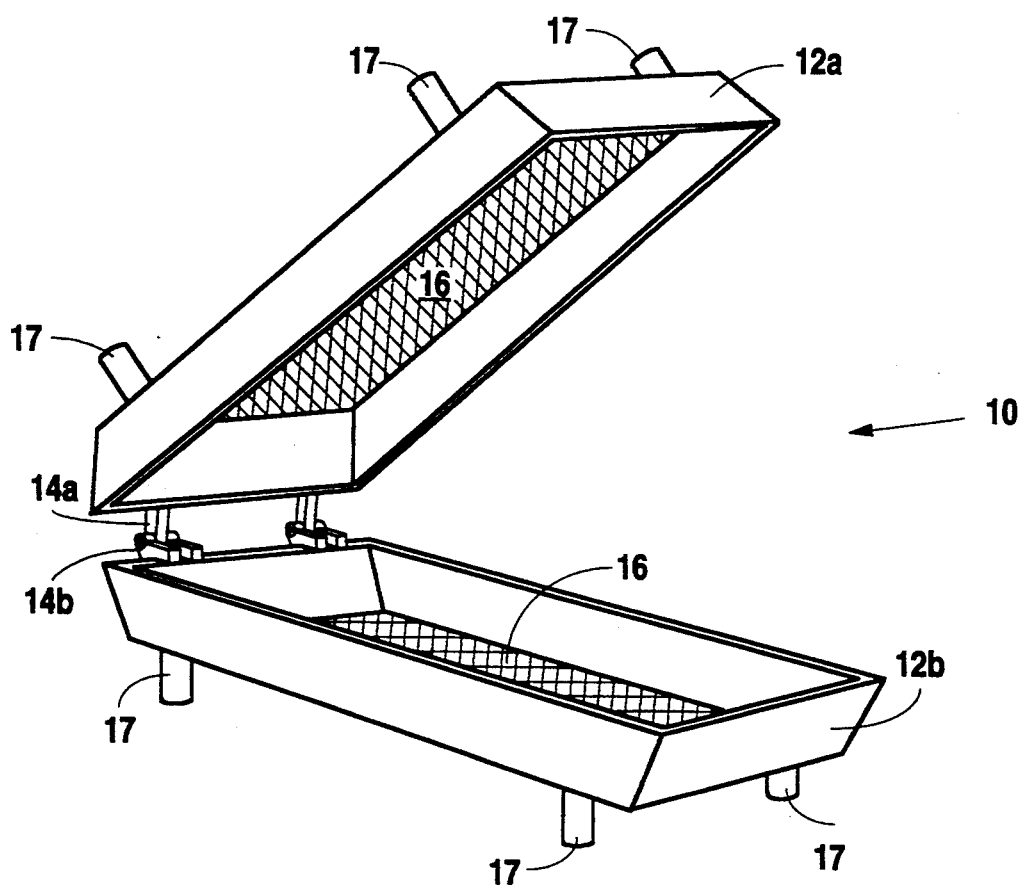
FIG. 1 is a perspective view of the articulator of the present invention.

Referring to FIG. 1, a perspective view is shown of the dental articulator 10 of the present invention. The articulator comprises upper and lower trays 12a and 12b, respectively, which are secured by hinge members 14a and 14b. The hinge members 14a and 14b each comprises a shoulder 15a and 15b, respectively, to limit rotation of the trays to a parallel orientation shown in FIG. 4. The upper tray 12a comprises a grid having a plurality of apertures 16 which are arranged in a spaced pattern. The lower tray 12b also comprises a grid having a plurality of apertures. These apertures are used for aligning pins in the impression of the appropriate teeth, as described in greater detail below. Each of the trays 12a and 12b are provided with a plurality of feet 17 which prevent the pins from being dislodged from the apertures when the articulator is placed on a work surface.

Figure 2:
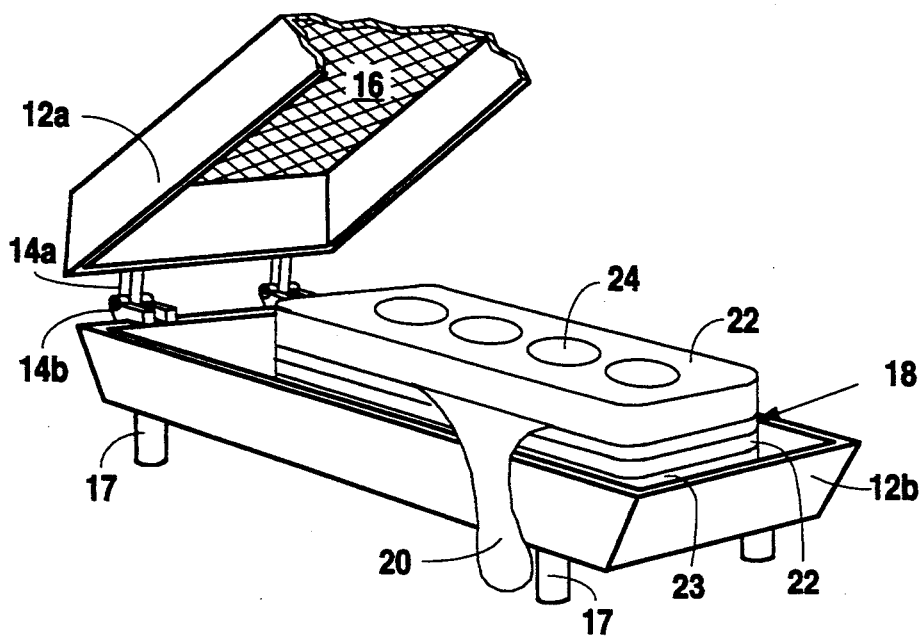
FIG. 2 is a perspective view of the articulator of the present invention with a dental impression received therein.

Referring to FIG. 2, a negative impression 18 of a tooth pattern is shown in the lower tray 12b of the articulator. The impression 18 is normally made in a dentist's office by having a patient bite on a plastic tray 20 upon which a quantity of a polymer dental impression material 22 is carried. When the impression is removed from the patient's mouth, a plurality of tooth impressions 24 remain in the polymer material. These tooth impressions are typically filled with a die stone material to form a positive model of the patient's teeth for purposes of constructing dental prothesis. The impression 18 is secured in the lower tray 12b by placing a quantity of dental plaster into the negative impression of the opposing teeth and also pouring a quantity of dental plaster 23 into the lower tray. The impression is then placed in the tray to allow the two quantities of dental plaster to mix and harden into an integrated dental plaster model base.

Because the dental plaster is initially in a liquified state is it necessary to provide means to prevent the dental plaster from leaking through the apertures 16. In the preferred embodiment of the present invention, this is accomplished by placing a liner 25, illustrated in FIGS. 3a and 3b, adjacent the apertures in each of the trays. In the embodiment of the invention illustrated in FIG. 3a, the liner 25 is shown in the inner surface of the tray. However, in an alternate embodiment of the invention, shown in FIG. 3b, the liner can be placed on the outer surface of the tray 12a or 12b. The liner can be fabricated from a thin sheet of pliable plastic which prevents the passage of liquids but which can be pierced by the dowel pins which are inserted into the apertures 16, as discussed below. An alternate means for preventing passage of the dental plaster through the apertures can be provided by molding the trays such that a thin membrane of plastic material seals each of the apertures. These seals can be stretched during the initial placement of the pins and then can be perforated by the pins once the final location has been established.

In the system of the present invention, a plurality of pins 26 are positioned at the locations corresponding to the tooth impressions 24 with the upper and lower trays in the closed position shown in FIG. 3. The upper tray 12a is then rotated upward as shown in FIG. 4, without disturbing the location of the pins in the apertures 16 of the upper tray 12a. The pins are held somewhat loosely when initially placed in the apertures 16 to determine the optimum locations corresponding to the teeth of interest. Therefore, it is necessary that the pins not be disturbed until they are more securely supported in the apertures. As can be seen in FIG. 5, the spacing feet 17 keep the pins from coming into contact with the working surface 19, thereby preventing the pins from being dislodged from the apertures in the tray 12a.

Figure 6:
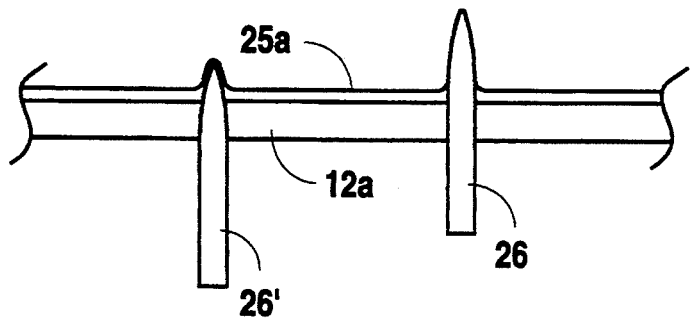
FIG. 6 is a side view of a portion of one of the trays showing the dowel pins being gripped in the apertures of the tray.

FIG. 6 is an illustration of a method of temporarily placing the pins 26 in the apertures in one of the articulator trays. Referring to FIG. 6, a pin 26' is shown in the initial placement position wherein the tapered portion of the pin in placed in the aperture to loosely support the pin in the upper tray 12a. In the embodiment shown in FIG. 6, a membrane liner 25a to prevent leakage of the dental plaster is shown on the outside tray. In the preferred embodiment of the invention, the trays 12a and 12b are formed from a plastic material and, therefore, the portion of the trays surrounding the apertures is somewhat flexible. With the pin partially inserted into the aperture, the membrane is stretched slightly but not punctured. Once the position of the pin has been verified, the pin is moved to the position shown by pin 26 in FIG. 6 with the membrane 25a being punctured and the pin held in the aperture by friction resulting from compression of the plastic material as the pin is forced into the aperture.

Figure 7:
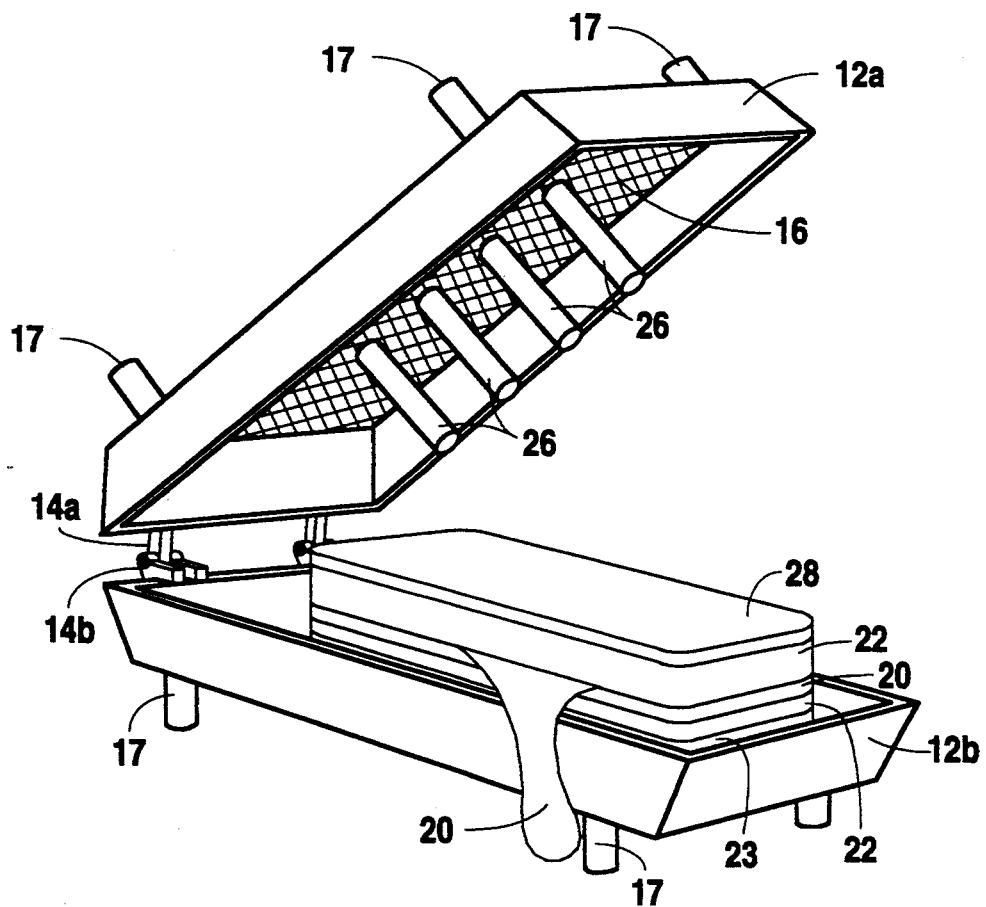
FIG. 7 is a perspective view of the dental articulator with the dowel pins being positioned in the apertures of the upper tray and a quantity of die stone placed in the negative dental impression.
Figure 8:
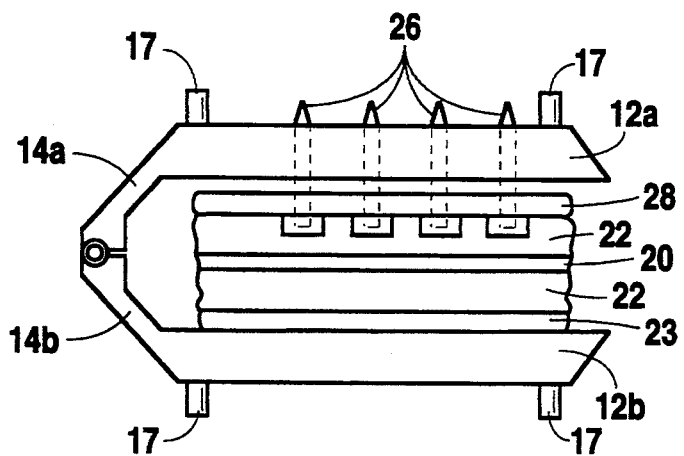
FIG. 8 is a side view of the dental articulator of the present invention showing the opposing trays aligned with the pins inserted into die stone in the negative dental impression.
Figure 9:
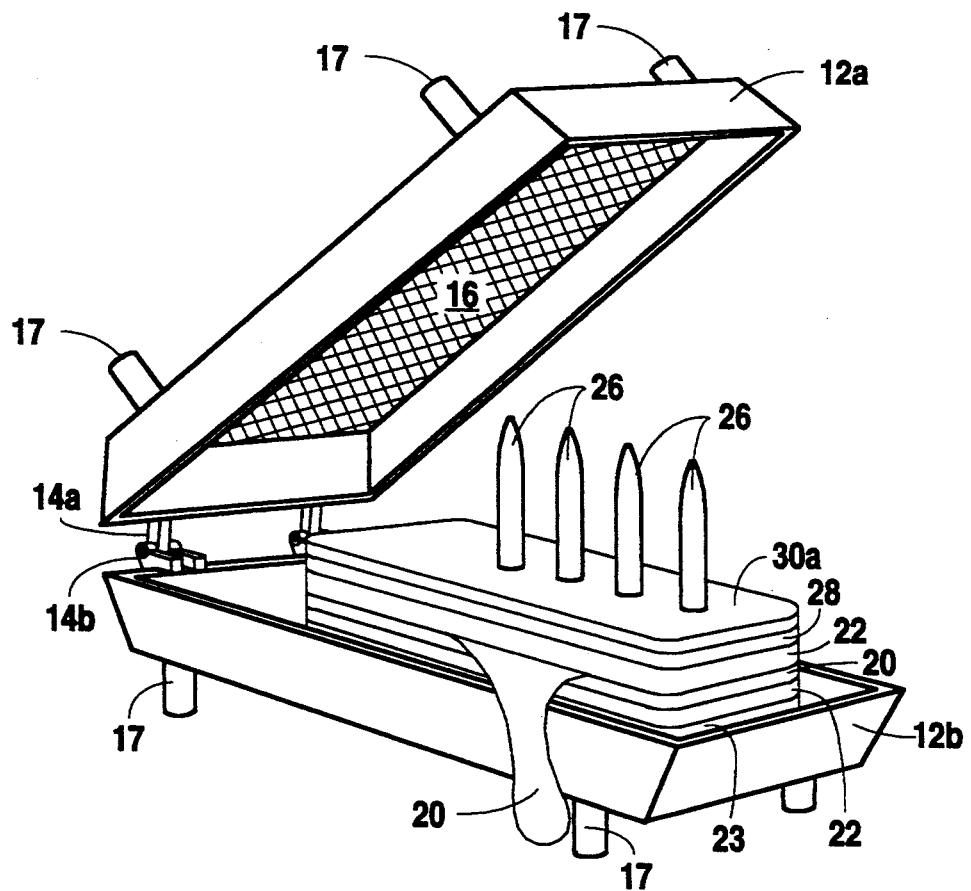
FIG. 9 is a perspective view of the dental articulator illustrated in FIG. 8 showing the upper tray rotated away with the dowel pins being retained in the hardened die stone.

With the upper tray 12a in the position shown in FIG. 7, a quantity of die stone 28 is placed in the impression to create a positive model of the teeth. The upper tray 12a is then rotated to the position shown in FIG. 8 with the pins 26 being inserted into the individual teeth impressions at the precise locations determined in FIG. 4. The articulator trays are left in the position shown in FIG. 8 for a predetermined length of time during the which the die stone 28 hardens. The upper tray 12a is then rotated upward with the individual pins remaining in the die stone 28, as shown in FIG. 9, and a separator is applied to the surface of die stone.

Figure 10:
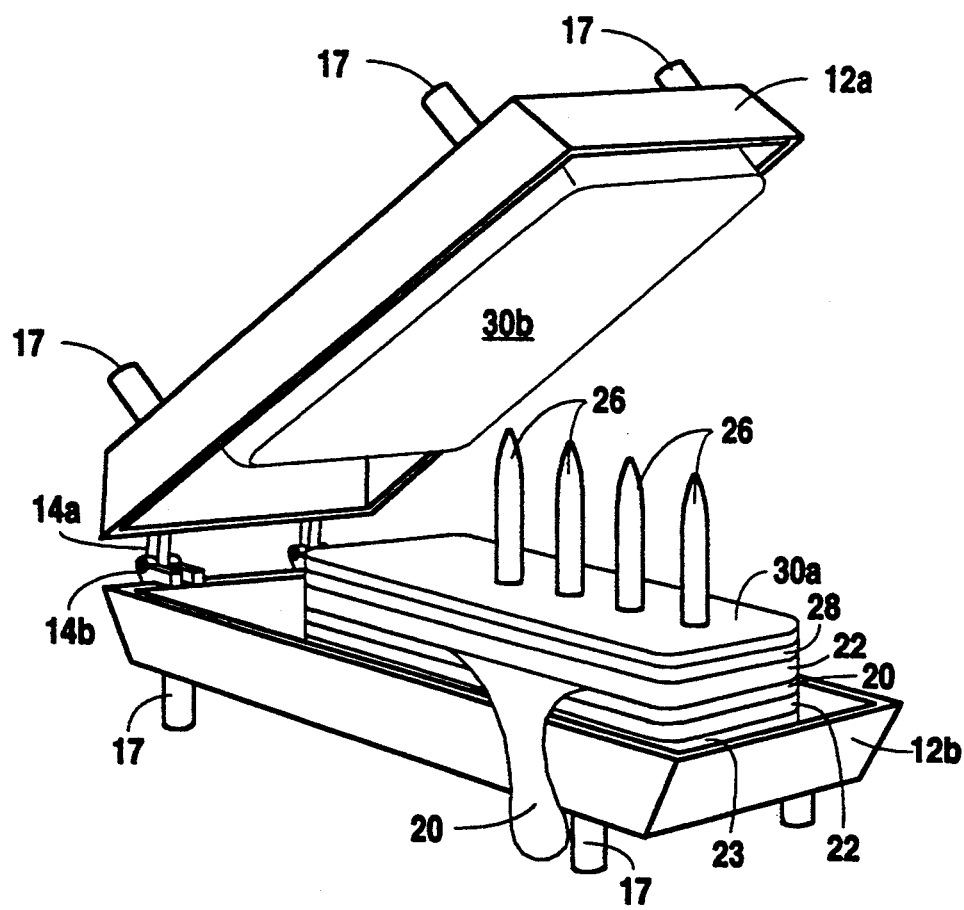
FIG. 10 is a view of the dental articulator of FIG. 6 showing the application of a quantity of plaster to the dental model and tray.
Figure 11:
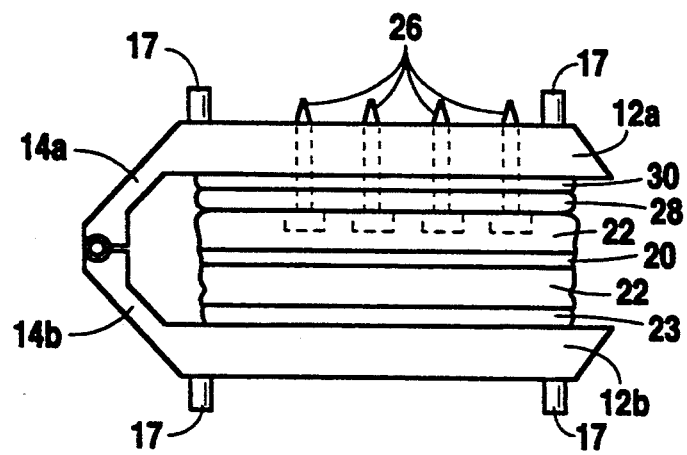
FIG. 11 is a side view of the dental articulator of the present invention showing the opposing trays aligned with the various layers of plaster applied to complete the construction of the dental model.
Figure 12:
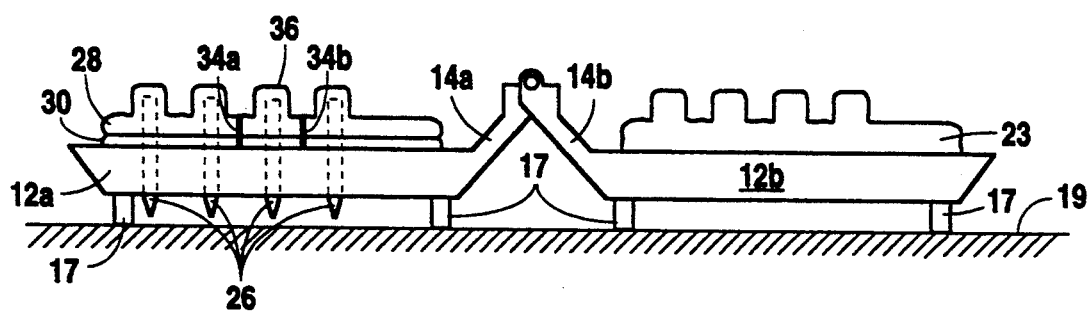
FIG. 12 is a side view of the completed dental model separated from the impression with half of the model contained in each of the trays.
Figure 13:
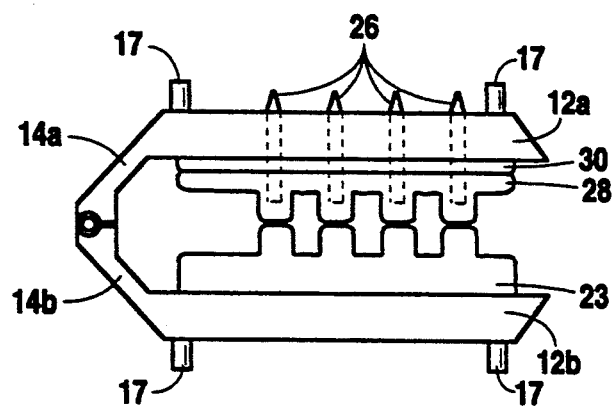
FIG. 13 is a side view of the dental articulator showing the respective halves of the dental model in the opposing trays of the articulator to allow a technician to check the registration of an artificial tooth.

Referring to FIG. 10, a quantity of dental plaster 30a is shown applied to the upper surface of the die stone 28. An additional quantity of dental plaster 30b is placed in the upper tray 12a. The upper and lower trays are then aligned as shown in FIG. 11 with the quantities of dental plaster 30a and 30b forming a single layer of dental plaster illustrated generally by reference numeral 30. After the dental plaster 30 has hardened, the dental model can be separated to remove the impression 22. The respective halves of the dental model will be contained in the trays 12a and 12b of the articulator as shown in FIG. 12. The working model of the tooth of interest 36 can be removed by cutting the die stone on either side of the tooth, as illustrated by cut lines 34a and 34b, and then pushing the appropriate pin to dislodge the tooth model from the overall model. The dental technician to proceed with fabrication of an artificial tooth or prosthetic in a conventional manner. Once the artificial tooth or prosthetic has been fabricated it can be reinserted into the model to check the articulation of the bite to verify that the registration of the artificial tooth is correct.

The articulator system provided by the present invention offers numerous advantages over the prior art. Using the articulator of the present invention, it is not necessary to drill holes in the dental plaster for purposes of inserting the pin. Furthermore, no glue is used for pins or articulation in the present invention. In the system of the present invention, the negative impression is not removed from the articulator during any of the intermediate steps required to secure the pins within the models, thereby maintaining exact relationship of models to each other as recorded by the impression.

The articulator of the present invention also offers advantages related to newer methods for making crowns wherein the crown is baked on a refractory model. In such methods, the model is constructed using a refractory die material and high temperature dowel pins are used in place of the conventional dowel pins. The refractory die material does not have as high a viscosity as conventional die stone. Because of the difficulty of placing the dowel pins in the refractory die material, dental technicians are often reluctant to use dowel pins. Therefore, the accuracy of the model is compromised. The articulator of the present invention, however, allows the pins to be placed accurately and maintained during the time the refractory die is curing. Thus the resulting model has a very high degree of accuracy, resulting in a minimal amount of adjustment to be performed by the dentist when seating the crown.

Although the method and apparatus of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

What is claimed is:

1. A dental articulator, comprising:
   a first tray for containing a quantity of dental plaster during and after casting of a dental model having teeth, said first tray comprising a grid having a plurality of apertures defining multiple pin locations for receiving a plurality of dental pins, said pin locations being spaced such that an individual pin may be held in the casting of each individual tooth of said dental model; and
   a second tray for receiving a quantity of dental plaster during and after casting a dental model, said second tray comprising a grid having a plurality of apertures defining multiple pin locations for receiving dental pins, said second tray being hingedly secured to said first tray to allow articulating movement of said first and second trays with respect to each other.

2. The dental articulator according to claim 1, further comprising means for preventing passage of dental plaster through said apertures in said first and second trays during casting of a dental model.

3. The dental articulator according to claim 2, further comprising a plurality of pins received in said apertures in one of said trays, said trays comprising spacing means to prevent said pins from being dislodged from said apertures in said one of said trays when said articulator is placed on a work surface.

4. A dental articulator, comprising:
   a first tray for containing a quantity of dental plaster, said first tray comprising a plurality of apertures in a spaced pattern for receiving a plurality of dental pins;
   a second tray for receiving a quantity of dental plaster, said second tray comprising a plurality of apertures, said second tray being hingedly secured to said first tray to allow articulating movement of said first and second trays with respect to each other;
   means for preventing passage of dental plaster through said apertures in said first and second trays, said means for preventing passage of said plaster through said apertures comprising a membrane placed on at least one surface of said first and second trays; and
   a plurality of pins received in said apertures in one of said trays, said trays comprising spacing means to prevent said pins from being dislodged from said apertures in said one of said trays when said articulator is placed on a work surface.

5. The dental articulator according to claim 4, wherein said membrane is placed on an outer surface of said first and second trays.

6. The dental articulator according to claim 4, wherein said membrane is placed on an inner surface of said first and second trays.

7. A dental articulator, comprising:
   a first tray .for containing a quantity of dental plaster during and after casting a dental model having teeth, said first tray comprising a plurality of apertures in a spaced pattern for receiving a plurality of dental pins, said apertures being spaced such that an individual pin may be held in the casting of each individual tooth of said dental model; and
   a second tray for receiving a quantity of dental plaster, said second tray comprising a plurality of apertures, said second tray being hingedly secured to said first tray to allow articulating movement of said first and second trays with respect to each other; and
   a plurality of pins received in said apertures in one of said trays, said first and second trays comprising spacing means to prevent said pins from being dislodged from said apertures when said articulator is placed on a work surface and further comprising means for preventing passage of dental plaster through said apertures in said first and second trays, said means for preventing passage of said plaster through said apertures comprising a membrane placed on a least one surface of said first and second trays.

8. The dental articulator according to claim 7, wherein said membrane is placed on an outer surface of said first and second trays.

9. The dental articulator according to claim 7, wherein said membrane is placed on an inner surface of said first and second trays.

10. A dental articulator, comprising:
a first tray to hold dental impression material for casting a dental model having teeth;
a holding means comprising a second tray wherein said holding means independently secures each tooth of the dental model wherein said second tray has a plurality of regularly spaced apertures for receiving a plurality of pins to hold the dental model, said apertures being spaced such that an individual pin may be held in the casting of each individual tooth of said dental model, said holding means further comprising a membrane covering said apertures, the membrane being compressed when a pin is inserted into a selected aperture thereby providing a frictional force releasably holding the pin therein; and
a positioning means for repeatably positioning said first and second trays in precise alignment with one tray above the other tray.

11. The dental articulator according to claim 10, wherein the holding means is independent of any tray walls so that after curing of the casting a selected tooth model may be cut from the dental casting while the overall casting remains secured to the second tray.

12. The dental articulator according to claim 10 said holding means further comprising portions of said tray surrounding said apertures, wherein the surrounding portions flex when a pin is inserted into an aperture thereby providing a frictional force releasably holding the pin in the aperture.

13. The dental articulator according to claim 10, wherein the positioning means comprises a hinge having hinge members, the hinge rotatably securing said first and second trays, and each hinge member having a shoulder that limits the rotation of said trays to an orientation with one tray above and essentially parallel to the other tray so that pins may be embedded to a predetermined depth in the uncured casting.

14. The dental articulator according to claim 10: wherein the second tray is also adapted for containing dental impression material so that said impression material may be received in the second tray and a second dental model having teeth may be cast therein; and wherein the first tray also provides a holding means so that a pin may be inserted and held in each tooth of the second dental model.

15. A dental articulator, comprising:
a first tray for containing dental impression material and for casting a dental model into said material;
a holding means comprising a second tray having a plurality of regularly spaced apertures, said apertures being spaced such that an individual pin may be held in the casting of each individual tooth of said dental model, said holding means further comprising a membrane coveting said apertures, the membrane being compressed when a pin is inserted into an aperture thereby providing a frictional force releasably holding the pin in said aperture, and wherein the holding means is independent of the tray walls;
a positioning means for repeatably positioning said trays in precise alignment;
wherein the second tray is also adapted for containing dental impression material so that a second dental model having teeth may be cast in the second tray; and
wherein the first tray also provides a holding means so that a pin may be inserted and held in each tooth of the second dental model.

* * * * *